(12) United States Patent
Shiraishi et al.

(10) Patent No.: US 7,678,404 B2
(45) Date of Patent: Mar. 16, 2010

(54) UBIQUINONE-ENRICHED FOODS

(75) Inventors: Tadayoshi Shiraishi, Hyogo (JP); Masayuki Abe, Hyogo (JP); Takeshi Kawashima, Hyogo (JP); Toshinori Ikehara, Hyogo (JP)

(73) Assignee: Kaneka Corporation, Osaka-shi (JP)

( * ) Notice: Subject to any disclaimer, the term of this patent is extended or adjusted under 35 U.S.C. 154(b) by 1000 days.

(21) Appl. No.: 10/501,685

(22) PCT Filed: Jan. 20, 2003

(86) PCT No.: PCT/JP03/00396

§ 371 (c)(1),
(2), (4) Date: Apr. 4, 2005

(87) PCT Pub. No.: WO03/061396

PCT Pub. Date: Jul. 31, 2003

(65) Prior Publication Data

US 2005/0181109 A1  Aug. 18, 2005

(30) Foreign Application Priority Data

Jan. 18, 2002  (JP)  ............................. 2002-009739

(51) Int. Cl.
*A23D 7/00* (2006.01)
*A23D 9/00* (2006.01)
*A23L 1/30* (2006.01)

(52) U.S. Cl. .................. 426/601; 424/451; 426/72; 426/531; 426/651

(58) Field of Classification Search ................ 426/601, 426/531, 651, 72; 424/451
See application file for complete search history.

(56) References Cited

U.S. PATENT DOCUMENTS

| 5,258,179 | A | 11/1993 | Bracco et al. |
| 5,989,583 | A | 11/1999 | Amselem |
| 6,441,050 | B1 | 8/2002 | Chopra |
| 6,616,942 | B1 * | 9/2003 | Udel ........................... 424/451 |
| 2003/0113307 | A1 * | 6/2003 | Selzer ........................ 424/94.1 |

FOREIGN PATENT DOCUMENTS

| EP | 0 424 679 B1 | 5/1991 |
| EP | 0 803 201 A2 | 10/1997 |
| EP | 0 956 854 A1 | 11/1999 |
| JP | 35-8095 | 6/1960 |
| JP | 54-92616 A | 7/1979 |
| JP | 57-142911 A | 9/1982 |
| JP | 3-167293 A | 7/1991 |
| JP | 4-278066 A | 10/1992 |
| JP | 10-45614 A | 2/1998 |
| JP | 10-147523 A | 6/1998 |
| JP | 2000-197445 A | 7/2000 |
| JP | 2000-302677 A | 10/2000 |
| JP | 2003-88330 A | 3/2003 |
| JP | 2003-561352 | 5/2007 |
| WO | WO 88/03365 A | 5/1988 |
| WO | WO 96/38047 | 12/1996 |
| WO | WO 98/21984 | 5/1998 |
| WO | WO 98/56368 A | 12/1998 |
| WO | WO 01/91590 A1 | 12/2001 |
| WO | WO 02/17879 A1 | 3/2002 |

OTHER PUBLICATIONS

Supplementary European Search Report from Application No. EP 03 70 1783, dated Feb. 25, 2005, 3 pages.
Patent Cooperation Treaty International Preliminary Examination Report (PCT Article 36 and Rule 70), From Corresponding International Application No. PCT/JP2003/000396, Dated Dec. 25, 2003, 6 pages.
International Search Report From Corresponding International Application No. PCT/JP03/00396, Dated Apr. 30, 2003, 2 pages.
Weber, C. et al., "Antioxidative Effect of Dietary Coenzyme $Q_{10}$ in Human Blood Plasma," *Vitamin and Nutrition Research*, 1994, vol. 64, No. 4, pp. 311-315.
Sakurai, Yoshito et al., "Shokuhin-Betsu Tenkabutsu Youran," (Handbook of Additives for Various Kinds of Food), Mar. 31, 1970, pp. 85-87.

* cited by examiner

*Primary Examiner*—Brent T O'Hern
(74) *Attorney, Agent, or Firm*—Connolly Bove Lodge & Hutz LLP; Burton A. Amernick

(57) ABSTRACT

To provide a ubiquinone supplementation food which is obtained by adding a composition containing ubiquinone and an oil/fat; an edible oil/fat composition which contains ubiquinone; a process for producing a ubiquinone supplementation food which comprises dissolving ubiquinone in an oil/fat under heating, and adding the obtained mixture to a food material; a method for preventing precipitation and/or localization of ubiquinone in a food which comprises producing a food by dissolving ubiquinone in an oil/fat under heating and adding the obtained mixture to a food material; and a method for supplying ubiquinone which comprises ingesting said foods.

4 Claims, No Drawings

UBIQUINONE-ENRICHED FOODS

RELATED APPLICATIONS

This application is a nationalization of PCT Application No. PCT/JP03/00396 filed Jan. 20, 2003. This application claims priority from Japanese Patent Application No. 2002-9739 filed on Jan. 18, 2002.

TECHNICAL FIELD

The present invention relates to a ubiquinone-enriched food which can supply ubiquinone, a substance indispensable to the living body but liable to be decreased and become short of requirements due to aging and stresses, with ease through ingestion in the same ways as the ordinary foods in daily living, uses thereof, and processes for producing said food.

BACKGROUND ART

Ubiquinone is a benzoquinone derivative distributed broadly in the living world. Ubiquinone is localized in mitochondria, lysosomes, Golgi bodies, microsomes, peroxisomes, cell membranes, etc., are substances indispensable for the maintenance of biological functions as constituents of the electron transport system, and are known to be involved in activation of ATP production, antioxidant activity in the living body, and membrane stabilization. Since ubiquinone is not only supplied from diets but also biosynthesized in the body, it might be considered that the necessary amount of ubiquinone is available in the normal state but it is known that actually the ubiquinone content in the body is markedly decreased due to aging and various stresses to which the living body is subjected.

For example, it is reported that whereas the ubiquinone content in the human heart in the 19 to 21 years of age is 110.0 µg/g, the content is drastically reduced to less than one-half, namely 47.2 µg/g, in the 77 to 81 years of age [Kalen, A. et al., Lipids, 24, 579-584 (1989)]. Moreover, the ubiquinone content in plasma is decreased in uremic patients, patients under chronic hemodialysis treatment, and patients with various allergic diseases as compared with healthy persons [Triolo, L., Nephron, 66, 153-156 (1994); Folkers, K., BioFactors, 1, 303-306 (1988)]. In patients with hyperlipemia, the ubiquinone content in the LDL cholesterol fraction is decreased [Kontush, A., et al., Atherosclerosis, 129, 119-126 (1997)]. Furthermore, it has been pointed out that administration of cholesterol synthesis inhibitors which are in common use today as therapeutic drugs for hypercholesterolemia inhibits the biosynthesis of ubiquinone as well, causing depressions in ubiquinone concentration in tissues [E. L. Appelkvist et al., Clinical Investigator, 71, S97-S102 (1993)]. In addition, decreases in the tissue concentration are suspected under conditions favoring production of peroxides in the living body, such as strenuous exercises or overfatigue. Decreases in the ubiquinone content in the body characteristically lead to depressions in ATP productivity and cardiac function, decreased resistance to oxidation stress, and instability of the biomembranes, thus being deleterious to health.

To make up for a shortage of ubiquinone is instrumental for promoting energy production in mitochondria, enhancing the antioxidant capacity of the living body, and maintenance of homeostasis. In fact, elevation of the cardiac function due to administration of ubiquinone has been reported [Kishi, T. et al., Clin. Investg., 71, S71-S75 (1993)]; ameliorating efficacy in cardiac diseases such as congestive heart failure, angina pectoris, myocardial infarction, etc. by ubiquinone [Singh, R. B. et al., Inter. J. Cardiology, 68, 23-29 (1999), Singh, R. B. et al., Cardiovasc. Drugs Ther., 12, 347-353 (1998)]; preventive and ameliorative efficacy in atherosclerosis, hypertension, diabetes, neoplastic diseases, periodontal diseases, and allergies [Singh, R B. et al., Atherosclerosis, 148, 275-282 (1999), Digiesi, V., et al., Curr. Therap. Res., 51, 668-672 (1992), Kishi, T., et al., Journal of Dental Health, 43, 667-672 (1993), Shimura Y., et al., Rinsho-to-Kenkyu, 58, 1349-1352 (1981)]; reproductive performance-improving effect, inhibition of oxidation of LDL cholesterol, dialysis frequency-reducing effect in renal dialysis patients, nonspecific immunity-potentiating effect, and the like are known [Stocker et al., Mol. Aspects Med., 18, S85-S103 (1997), Lippa, S., Mol. Aspects Med., 15, S213-S219 (1994)]. Furthermore, ubiquinone is already in use clinically as a therapeutic drug for the palpitation, short breadth, and anasarca arising from congestive heart failure or mild heart diseases.

As means for supplying the ubiquinone which tend to become decreased and fall short of the requirements due to aging and stresses despite their being indispensable for the maintenance of biological functions as mentioned above, it has already been practiced to supply this substance as a drug or as a food supplement in the form of tablets or capsules but for healthy or semi-healthy persons in whom deficiencies are slight and unqualified for medical care, and the like persons, it is more convenient to take this substance in the same ways as the ordinary food than taking it in the form of tablets or capsules. Furthermore, in the case of foods, it is possible to produce foods having various flavors and forms, thus offering the great advantage that the consumer may ingest the food repeatedly without being bored.

Ubiquinone is known to occur broadly in many ordinary foodstuffs of the animal or vegetable origin, such as meats, fish meats, cereals, vegetables, fruits, dairy products, and eggs, the content is generally low except in beef in which it is as high 30 µg/g, and the like. For example, the said content is as low as about 1.5 µg/g in hen's eggs, about 1.1 µg/g in wheat breads, and about 0.52 µg/g in potatoes, so that the daily ingestion from the usual diets is about 3 to 5 mg. Furthermore, the absorption rate of ubiquinone after oral ingestion is low, so that with the ordinary foods taken in the usual manner, it is not easy to sufficiently supply ubiquinone in the living body which is liable to be decreased due to various stresses.

In such cases, if a ubiquinone-enriched food is available, improvements in its absorption rate could be expected from the interaction with the food component and, hence, it can be considered that ubiquinone, which is liable to be fall short of the requirements, can be supplied with ease. However, partly because ubiquinone had been classified as a drug with the use thereof as food being restricted in Japan, only a few ubiquinone-enriched foods are available today. The only exceptions are Japanese Kokai Publication Hei-03-167293 "the method of preventing oxidation of oils/fats and oil/fat-containing foods", Japanese Kokai Publication 2000-197445 "Freshness-keeping agent for animal meats, fish meats, and processed foods thereof", Japanese Kokai Publication Hei-10-45614 "Foods for diet therapy and pharmaceutical products for inhibiting blood coagulation", and Japanese Kohyo Publication 2001-504343 "Ubiquinone-containing non-alcoholic beverages". Disclosed in Japanese Kokai Publication Hei-03-167293 relates to a technology for preventing oxidation of oils/fats which comprises concurrent admixing of ubiquinone, ascorbic acid, and a natural emulsifier, but there is no disclosure of the concept of a ubiquinone-enriched food for supplementation use. Japanese Kokai Publication 2000-197445 is concerned with the use of ubiquinone as a freshness-keeping agent for animal meats, fish meats, and processed foods thereof and the level of addition is so low that substantially no supplementation effect can be expected. Disclosed in Japanese Kokai Publication Hei-10-45614 is a food for diet therapy for inhibiting blood coagulation which comprises using a ubiquinone-rich corn germ oil, but its ubiquinone content is only about 0.0007 to 0.0008% by weight (hereinafter referred to briefly as %), thus is insufficient to meet the requirements for making up for deficiencies in ubiquinone. Moreover, this technology is concerned with utilization of the ubiquinone occurring inherently in corn germ oil, and does not describe the concept of enrichment with ubiquinone. Japanese Kohyo Publication 2001-504343 discloses a technology of solubilizing ubiquinone with polyoxyethylene sorbitan monooleate but the use of such a nonionic surfactant has the risk for causing hemolysis, mucosal irritation, mucosal defect and the like and, in many cases, utilization thereof in food applications is actually hesitated.

Under such circumstance, as the food which can supply ubiquinone, a substance indispensable to the living body but liable to be decreased and fall short of requirements due to aging and stresses, one may reasonably contemplates a food sufficiently enriched with ubiquinone, improved in absorption rate, and having a pleasing flavor.

SUMMARY OF THE INVENTION

The object of the present invention is to provide a food containing ubiquinone in uniformly dispersed state, thus permitting ingestion of ubiquinone in the same ways as the ordinary foods, uses thereof, and a method for producing said food in dairy living.

The present inventors have been interested in the functions of ubiquinone and conducted a series of research and investigation on a ubiquinone-enriched food. However, mere addition of ubiquinone to a substrate food may hardly provide a uniform solution or dispersion of ubiquinone, and even if the ubiquinone has been uniformly dissolved in a substrate food, it tends to separate out to localize during storage, thus presenting problems in terms of flavor and appearance of foods and causing failures to obtain satisfactory foods. This is due to the insolubility of ubiquinone in water and the remarkably low solubility of ubiquinone in oils/fats.

However, the research done by the present inventors led to the finding that a composition containing ubiquinone and an oil/fat may retain ubiquinone in a uniformly dissolved and dispersed state even if the level of addition of ubiquinone is over the solubility limit in the oil/fat.

By utilizing such a composition containing ubiquinone and an oil/fat, a uniform dissolution or dispersion of ubiquinone in the substrate food can be insured without entailing precipitation and localization of the ubiquinone in a food during storage and the resulting food is fully acceptable in flavor, texture, and appearance. As a result of further investigations, the present inventors have completed the present invention.

Thus, the present invention relates, in a first aspect, to
a ubiquinone supplementation food
which is obtainable by adding a composition containing ubiquinone and an oil/fat.

As the preferable embodiment, there may be mentioned:
(1) The above-mentioned ubiquinone supplementation food,
which contains 0.001 to 50% by weight of ubiquinone based on the total weight of the food;
(2) The above-mentioned ubiquinone supplementation food,
which contains 0.01 to 50% by weight of ubiquinone based on the total weight of the oil/fat;
(3) The above-mentioned ubiquinone supplementation food,
wherein the oil/fat has a melting point of not lower than 20° C.;
(4) The above-mentioned ubiquinone supplementation food,
wherein the composition containing ubiquinone and an oil/fat is obtainable by dissolving ubiquinone in the oil/fat having a melting point of not lower than 20° C. under heating, and solidifying or plasticizing the obtained mixture, or preparing the obtained mixture into an oil-in-water emulsion or a water-in-oil emulsion;
(5) The above-mentioned ubiquinone supplementation food,
wherein the oil/fat has a melting point of below 20° C.;
(6) The above-mentioned ubiquinone supplementation food,
wherein the composition containing ubiquinone and an oil/fat is obtainable by dissolving ubiquinone in the oil/fat having a melting point of below 20° C. under heating, and preparing the obtained mixture into an oil-in-water emulsion;
(7) The above-mentioned ubiquinone supplementation food,
which is at least one species selected from the group consisting of milk, dairy products, sauces, breads, pies, cakes, confections, roux, seasoning liquors, ice confections, noodles, processed foods, boiled rice preparations, jams, canned foods, and beverages;
(8) The above-mentioned ubiquinone supplementation food,
which further contains an antioxidant and/or an edible color; and
(9) The above-mentioned ubiquinone supplementation food,
wherein the antioxidant and/or edible color is at least one species selected from the group consisting of ascorbyl palmitate, ascorbyl stearate, catechin, lecithin, tocopherol, tocotrienol, lignan, and carotenoid.

The present invention relates, in a second aspect, to an edible oil/fat composition
which contains ubiquinone.

As the preferable embodiment, there may be mentioned:
(1) The above-mentioned edible oil/fat composition,
which contains 0.01 to 50% by weight of ubiquinone based on the total weight of the oil/fat composition;
(2) The above-mentioned edible oil/fat composition,
which further contains an antioxidant and/or an edible color; and
(3) The above-mentioned edible oil/fat composition,
wherein the antioxidant and/or edible color is at least one species selected from the group consisting of ascorbyl palmitate, ascorbyl stearate, catechin, lecithin, tocopherol, tocotrienol, lignan, and carotenoid.

The present invention relates, in a third aspect, to
a process for producing a ubiquinone supplementation food
which comprises dissolving ubiquinone in an oil/fat under heating, and adding the obtained mixture to a food material.

As the preferable embodiment, there may be mentioned:
(1) The above-mentioned process,
wherein the oil/fat has a melting point of not lower than 20° C., and the mixture to be added to a food material is obtainable by dissolving ubiquinone in said oil/fat under heating, and solidifying or plasticizing the resultant, or preparing the resultant into an oil-in-water emulsion or a water-in-oil emulsion; and (2) The above-mentioned process,
wherein the oil/fat has a melting point of below 20° C., and the mixture to be added to a food material is obtainable by dissolving ubiquinone in said oil/fat under heating, and preparing the obtained mixture into an oil-in-water emulsion.

The third aspect of the present invention also relates to
a ubiquinone supplementation food
which is obtainable by the above-mentioned process.

The present invention relates, in a forth aspect, to
a method for preventing precipitation and/or localization of ubiquinone in a food
which comprises producing a food by dissolving ubiquinone in an oil/fat under heating and adding the obtained mixture to a food material.

As the preferable embodiment, there may be mentioned:
(1) The above-mentioned method,
wherein the oil/fat has a melting point of not lower than 20° C., and the mixture to be added to the food material is obtainable by dissolving ubiquinone in said oil/fat under heating, and solidifying or plasticizing the resultant, or preparing the resultant into an oil-in-water emulsion or a water-in-oil emulsion; and (2) The above-mentioned method,
wherein the oil/fat has a melting point of below 20° C., and the mixture to be added to the food material is obtainable by dissolving ubiquinone in said oil/fat under heating, and preparing the resultant into an oil-in-water emulsion.

The present invention relates, in a fifth aspect, to
a method for supplying ubiquinone
which comprises ingesting the above-mentioned food.

In the following, the present invention is described in detail.

DETAILED DESCRIPTION OF THE INVENTION

The present invention relates to a ubiquinone supplementation food which is obtainable by adding a composition containing ubiquinone and an oil/fat. Foods prepared by adding ubiquinone and an oil/fat independently or foods containing ubiquinone but not containing an oil/fat fail to dissolve/disperse ubiquinone uniformly in the substrate food, thus it is difficult to prevent precipitation and localization of ubiquinone during food storage.

The food of the present invention is a food obtainable by enriching the food with ubiquinone at a level somewhere between the lower limit of preferably 0.0001% by weight, more preferably 0.001% by weight, still more preferably 0.01% by weight, most preferably 0.1% by weight, and the upper limit of preferably 50% by weight, more preferably 10% by weight, still more preferably 5% by weight, most preferably 2% by weight, as ubiquinone based on the total weight of the food. If the content of ubiquinone is below 0.0001% by weight based on the total weight of the food, the effect of supplying ubiquinone, which is liable to fall short of the requirements due to aging and stresses, may not be sufficient. Addition beyond 50% by weight may cause difficulties in attaining a substantially uniform dissolution or dispersion of ubiquinone in the food.

The food of the present invention contains ubiquinone at a level somewhere between the lower limit of preferably 0.01% by weight, more preferably 0.1% by weight, and the upper limit of preferably 50% by weight, and more preferably 20% by weight based on the total weight of the oil/fat. If the content of ubiquinone is below 0.01% by weight based on the total weight of the oil/fat, the effect of supplying ubiquinone, which is liable to fall short of the requirements due to aging and stresses, may not be sufficient. Addition beyond 50% by weight may cause difficulties in attaining a substantially uniform dissolution or dispersion of ubiquinone in the food.

The oil/fat for use in the present invention preferably has a melting point of not lower than 20° C., and more preferably not lower than 25° C. If the melting point is below 20° C., solid-liquid separation may occur during storage to make it difficult to obtain a uniform distribution of ubiquinone. However, oils/fats having a melting point of below 20° C. may also be used with advantage and, in this case, the ubiquinone-containing oil/fat composition is preferably provided in the form of an oil-in-water emulsion.

In this specification, any oil/fat having a melting point of not lower than 20° C. (i.e. any oil/fat which are solid at 20° C.) will hereinafter be referred to sometimes as "a solid fat", while any oil/fat having a melting point of below 20° C. (i.e. an oil/fat which is liquid at 20° C.) will be referred to sometimes as "a liquid oil".

In the present invention, where the oil/fat occurring in the food of the present invention is a mixture of two or more different species, such a mixture having a melting point of not less than 20° C. will also be referred to as a solid fat and such a mixture having a melting point of below 20° C. as a liquid oil.

The melting point of an oil/fat means a slip melting point. The slip melting point can be measured by the method described in the Standard Methods for Analysis of Oils and Fats (The Japan Oil Chemists' Society, 1996 edition).

The ubiquinone content in the food of the present invention can be determined by the method which comprises optionally subjecting the food to a suitable pretreatment such as milling and drying, subjecting said food or pretreated food further to 2 to 3 stirring/dissolving sessions, each for a duration of about 1 hour, in a suitable solvent (for example, about 10 parts by volume, relative to each part by dry weight of the food), such as chloroform/methanol (2/1, v/v) for extraction, removing the solvent from the extract by distillation to recover an extracted oil, dissolving this extracted oil in hexane, ethanol or the like, and, referring to the method for assay of ubidecarenone (another name of ubiquinone, being known as coenzyme $Q_{10}$) as described in A Commentary on the Pharmacopoeia of Japan, XIII (Hirokawa Shoten, 1996), subjecting the resulting solution to analysis by high performance liquid chromatography.

The species of foods of the present invention are not particularly restricted in ingredient, formulation, production process, form, use and the like but can be freely selected. However, in view of the characteristic of ubiquinone that it is freely soluble in hydrophobic solvents, foods rich in oil/fat are more advantageous because these can be enriched with ubiquinone at high levels and more uniformly. As preferred food according to the present invention, there may be mentioned edible oils/fats (edible oils/fats compositions), milk and dairy products, sauces, breads, pies, cakes, confections, roux, seasoning liquors, ice confections, noodles, processed foods, boiled rice preparations, jams, canned foods, beverages, and the like.

The term "edible oils/fats" in the context of the present invention means any of oils and fats of the vegetable origin, animal origin, microbial origin, fish origin or the like, that is predominantly composed of triglycerides, diglycerides, phospholipids, etc.; edible purified processed oils derived from the above oils by hydrogenation, fractionation, interesterification, or a suitable combination of such treatments, margarine products such as margarine, processed margarine, and fat spread; butters, shortenings, and the like. As the form of use of these oils/fats, there may be mentioned the forms for ingesting as they are, the forms for using in the processing of other foods, and the forms for eating together with other food ingredients, and the like. For example, such forms as cooking oils for frying, cooking oils for roasting, cooking oils for salads, and spray oils, etc. can be mentioned.

The "milk and/or dairy products" in the context of the present invention include not only the "milk", "dairy products", and "foods composed predominantly of milk or dairy products" as defined in the Japanese Ministry of Health regulations, namely milk, e.g. cow's milk, special cow's milk, sterilized goat's milk, partially defatted milk powder, processed milk, etc., various dairy products, e.g. creams, whipped creams, butters, butter oils, cheeses such as cheese and cheese-food, concentrated whey, ice creams, concentrated milk, whiteners, non-sweetened condensed milk, sweetened condensed milk, whole milk powders, cream powders, whey powders, protein concentrated whey powders, butter milk powders, sweetened milk powders, modified milk powders, fermented milks, lactic acid bacteria beverages, milk beverages, etc. and various fermentated dairy products, e.g. sour milks such as yogurt, alcohol fermentation milks such as kefir and koumiss, etc., but also synthetic creams, cheese-like foods, and the like.

As the "sauces" in the context of the present invention, there may be mentioned warm-prepared sauces such as white source, cream sauce, etc. and cold-prepared sauces such as mayonnaise, salad dressing, etc.

As the "breads" in the context of the present invention, there may be mentioned white bread, bread rolls, sweet baked buns, dainty-filled bread, steamed buns, doughnuts, and the like.

As the "pies" in the context of the present invention, there may be mentioned, apple pie, chestnut pie, pumpkin pie, meat pie, and the like.

The "cakes" in the context of the present invention include sponge cakes such as short cake and cake roll; butter cakes such as pound cake and fruit cake; chou cakes such as chou à la crème (cream puff) and èclair; fermented cakes such as savarin; cream jelly cakes such as unbaked cheesecake; dessert foods such as puddings and blancmange and the like.

As the "confections" in the context of the present invention, there may be mentioned Japanese style confections, snacks, chocolate and chocolate confections, fried confections, gums, candies. More particularly, said Japanese style confections include various fresh confections, e.g. rice cakes such as mochi and ohagi; steamed confections such as mushimanju, mushi-yohkan, and uirō; baked confections such as dorayaki, kintsuba, manju, geppei, and castella; cast confections such as yōkan, paste confections such as nerikiri, and gyūhi; semi-fresh confections, e.g. bean-jam confections such as ishigoromo, okamono such as monaka, baked confections such as chatsū; dry confections such as uchimono (hard-molded confections), e.g. rakugan, etc., and sweetened fermented beans; and the like: said snacks include cookies, biscuits, crackers, potato chips, corn chips, pretzel, nuts, popped corn, cereals, rice confections such as arare, okaki and senbei; and the like: said fried confections include karint ō and the like; said gums include sheet gums, balloon gums, sugar-coated gums, sugarless gums, and the like: said candies include hard candies such as drops and brittles, soft candies such as caramels and nougats; sugar-coated candies (kakemono) such as kompeito and jelly beans; refreshing sweets such as ramune-gashi; and the like.

As the "roux" in the context of the present invention, there may be mentioned roux blanc (white roux), roux blond (cream-colored roux), roux brun (brown roux), and the like.

The "seasoning liquors" in the context of the present invention means those liquids in general which are used for improving the flavor, shelf-life, processability, etc. of food in cooking/processing stages, and specifically, there may be mentioned bastes such as sesame baste, baste for roast eels, and baste for roast beef, pickling liquors, and the like.

As the "ice confections" in the context of the present invention, there may be mentioned ice-cream, sherbet (sorbet), ice candies, and the like.

The "noodles" in the context of the present invention mean any and all foods produced by noodling or otherwise dividing a dough or batter prepared by kneading a cereal flour with water or the like, specifically including udon, sōmen, hiya-mugi, chukamen (Chinese noodles), etc. all of which are prepared using wheat flour as the main raw material, various types of pasta such as spaghetti and macaroni which are based on durum semolina, soba based on buckwheat flour, Chinese rice noodles based on rice flour, harusame based on starch, and the like.

As the "processed food" in the context of the present invention, there may be mentioned processed meat products such as hams, sausages, and bacon hams, fish paste foods such as kamaboko and chikuwa, fried foods such as croquettes, pork cutlets, fried potatoes, and fried prawn, and frozen foods such as frozen entree, frozen animal products, and frozen farm products, and the like.

As the "boiled rice preparation" in the context of the present invention, there may be mentioned not only boiled rice but also takikomi gohan (boiled rice with other ingredients), fried rice, vinegar-seasoned rice, and the like.

As the "jams" in the context of the present invention, there may be mentioned foods prepared from fruits, such as mandarin orange, strawberry, apple, grape, Chinese gooseberry, and fig, vegetables such as pumpkin, flower petals of rose and the like, etc. by boiling them to suitable concentrations together with sugar.

As the "canned foods" in the context of the present invention, there may be mentioned canned or bottled foods prepared by filling meat, fish meat, fruits, vegetables, etc. inclusive of the corresponding processed foods, into containers, followed by clinching or capping.

As the "beverages" in the context of the present invention, there may be mentioned soy-milk, coconut milk, coffee drinks such as coffee with milk and café au leit; black tea drinks such as tea with milk and spiced tea (chai); carbonated beverages such as floats and cola drinks; flavored water such as lemon juice-containing mineral water; sports drinks; vegetable juice and fruit juice drinks based on various vegetables and fruits; and the like.

The present invention encompasses not only the foods exemplified above but also the corresponding foods subjected to multi-stage processing inclusive of coating, topping, folding or sandwiching, bean-jam enclosing, kneading-in, and the like.

The food of the present invention may be added with an antioxidant and/or an edible color in addition to ubiquinone. Addition of an antioxidant and/or an edible color enhances the heat stability and light stability of ubiquinone in the food and, at the same time, is useful to maintenance of the flavor of the food. As the antioxidant and/or edible color according to the present invention, there may be mentioned ascorbyl palmitate, ascorbyl stearate, catechin, lecithin, tocopherol, tocotrienol, lignan; and carotenoids such as astaxanthin, and lycopene; and the like, and these are preferably used. More preferred are ascorbyl palmitate, catechin, lecithin, and tocopherol. Commercial antioxidants and edible colors can be utilized. In the present invention, the level of addition with said antioxidant and/or edible color is preferably 0.001 to 10% by weight, still more preferably 0.005 to 1% by weight, based on the total weight of the food. If the level of addition is below 0.001% by weight, the effect of addition of the antioxidant and/or edible color may not be fully expressed. If added beyond 10% by weight, these additives tend to adversely affect the flavor and appearance of the food. In cases where the food of the invention is to be enriched not only with ubiquinone but also with these antioxidants and/or edible colors, the method for enrichment is not particularly restricted and may for example comprise mixing the above additive or additives into the substrate food together with the food ingredient containing ubiquinone and an oil/fat under stirring for dissolution. An alternative procedure comprises adding the antioxidant and/or edible color preliminarily to the oil/fat composition under stirring for uniform dissolution or dispersion and using the mixture as it is or adding it to a food for enrichment.

The present invention further relates to a method for supplying ubiquinone through ingesting a ubiquinone-enriched food. In accordance with the method of the present invention, said ubiquinone-enriched food of the present invention may be ingested in the same ways as the ordinary foods. Thus, except that the amount of food to be taken need to contain ubiquinone about 0.1 to 500 mg, more preferably about 1 to 200 mg per day, the mode, volume, and frequency of ingestion are not particularly restricted. If the level of ingestion is less than 0.1 mg, the effect that can be realized may be low, while ingestion in excess of 500 mg is sufficiently effective but may not be acceptable in economic terms.

The method of the invention can be applied to humans.

The method according to the present invention is more advantageous than the conventional method using a drug, a food supplement or the like because it permits expedient and long-term ingestion with ease, can be liberally controlled in the ingestion amount according to the prevailing circumstances, can be adapted to the gustatory and other sensory predilection which vary with different individuals, and the like. Furthermore, ubiquinone has the tendency of being better absorbed when ingested together with a food component, particularly a fatty ingredient than the case when it is taken alone and, from this point of view, too, it is a very meritorious method.

The process for producing the food of the present invention is now described.

The food of the present invention is not particularly restricted in its production process and can be produced by adding a composition containing the necessary amount of ubiquinone and an oil/fat in the course of production of the food. In a more preferred embodiment, ubiquinone is added together with the oil/fat and sufficiently stirred in the course of production of the food. By this procedure, a food containing ubiquinone uniformly at a high level can be easily produced. Moreover, by the concurrent addition of an oil/fat and ubiquinone, the precipitation and localization of ubiquinone which would occur often during storage can be prevented, with the result that the food obtained is quite satisfactory in flavor, texture, and appearance. Still more preferably, ubiquinone is dissolved in oils/fats under heating, and then the solution is cooled and homogenized to prepare an oil/fat composition, and the objective food is prepared using this composition. By this procedure, the localization of ubiquinone can be completely prevented. The oil/fat-containing food ingredient which can be used is not particularly restricted but a food ingredient with an oil/fat content of not less than 1% is preferred.

As preferred examples of such food ingredient, there may be mentioned edible oils/fats, butters, margarines, fat spreads, shortenings, cheeses, cheese foods, cheese-like foods, chocolates and chocolate-containing food ingredients, meats such as fish meat and animal meat, and processed products thereof, hen's eggs and processed egg products such as liquid egg, pulses such as soybeans, corns and peanuts, and processed pulse products thereof, powdered or otherwise processed food ingredients derived from sesame and cereals such as wheat and rice, e.g. wheat flour, barley flour, rye flour, rice flour, buckwheat flour, premix flour, wheat germs, soy milk, and so forth.

The preferable examples of said edible oil/fat are not particularly restricted provided that they are animals and plants oils/fats which are commonly used in foods. The above oils/fats include, for example, various vegetable oils such as rapeseed oil, soybean oil, sunflower seed oil, cottonseed oil, peanut oil, rice bran oil, corn oil, safflower oil, olive oil, kapok oil, sesame oil, evening primrose oil, palm oil, shea butter, sal fat, cacao butter, coconut oil, and palm kernel oil, and various animal oils/fats such as milk fat, beef tallow, lard, fish oil, and whale oil; various processed edible oils/fats derived from the above oils by hydrogenation, interesterification or the like; moreover, for example, medium-chain fatty acid triglycerides (MCT) such as triglycerides of fatty acids containing 6 to 12 carbon atoms, preferably 8 to 12 carbon atoms; partial glycerides (monoglycerides and diglycerides) of fatty acids, such as monoglycerides and diglycerides of fatty acids containing 6 to 18 carbon atoms, preferably 6 to 12 carbon atoms; and the like. These edible oils/fats are not particularly restricted either purified or unpurified. But for providing oils/fats which can be used for cooking or frying purposes as well in the same ways as the ordinary oils/fats, edible oils/fats having a smoke point of not lower than 170° C. may be used.

In said composition containing ubiquinone and an oil/fat for use in the production of the food according to the present invention, it is not indispensable that these components are completely dissolved. But in order that the final product food may be satisfactory in flavor, mouth-feel, appearance, and absorption rate, it is preferable that ubiquinone has been completely dissolved in the oil/fat. Accordingly, in dissolving ubiquinone in an edible oil/fat, it is preferable to add ubiquinone while heating the edible oil/fat to a temperature not lower than its melting point under stirring with care exercised so as not to be inhomogeneous.

Furthermore, in the case where the enrichment is carried out with ubiquinone over its solubility limit in the oil/fat, the preferred procedure using a solid fat comprises dissolving ubiquinone under heating and cooling the solution for solidification or kneading it for plasticization, or preparing an oil-in-water emulsion. The heating temperature is preferably not lower than the melting points of the solid fat and ubiquinone, and more preferably 50 to 70° C. The cooling procedure is preferably quenching to 20° C. or below for improved homogeneity. Moreover, the above solidified or plasticized oil/fat composition may be an anhydrous one or a water-in-oil emulsion. In either case, the ubiquinone can be uniformly incorporated in the solid fat which is a continuous phase. It is also permissible to add an emulsifier or the like which is conventionally used.

On the other hand, in cases where the enrichment is carried out with ubiquinone beyond its solubility limit in the oil/fat, the preferred procedure using a liquid oil comprises dissolving the ubiquinone in the oil/fat under heating and cooling the solution to prepare an oil-in-water emulsion. The heating temperature is preferably not lower than the melting point of ubiquinone, more preferably 50 to 70° C., and the cooling procedure is preferably quenching to 10° C. or below. By adopting an oil-in-water emulsion form, the ubiquinone can be uniformly incorporated in oil droplets dispersed uniformly in the water forming a continuous phase. To this oil-in-water emulsion, the emulsifier, thickener, etc., which are commonly used in oil-in-water emulsions, may optionally be added. In the case of an oil composition comprising a liquid oil alone instead of an oil-in-water emulsion, ubiquinone may remain uniformly dispersed immediately after cooling but chances are that as time goes by a solid-liquid separation takes place so that it is very likely that a bias occurs in the distribution of ubiquinone.

In the case where a ubiquinone-enriched food is produced by using the thus prepared edible oil/fat composition, the ubiquinone-enriched edible oil/fat composition may be added in the process of adding the oil/fat component in the production flow for said food. Particularly, since a kneadability characteristic is required in the production of foods based on wheat flour, e.g. breads, baked confections, etc., in particular, a plastic oil/fat composition obtainable from a solid fat is advantageous. Moreover, an oil-in-water emulsion composition may be added to an aqueous phase and, in this case, a liquid oil can be employed.

The food of the present invention may further contain, in addition to ubiquinone and said antioxidant and edible color, those additives which are conventionally added to ordinary foods as long as not adversely affecting the solubility, stability, absorbability of the ubiquinone. For example, there can be added vitamins such as vitamin A and vitamin D; inorganic salts such as common salt; sweeteners such as sucrose; food proteins such as milk protein; thickeners such as CMC; antioxidants such as butylhydroxytoluene (BHT); preservatives such as sorbic acid, its potassium salt, benzoic acid, its sodium or potassium salt; fruits; chocolate; and the like.

The ubiquinone for use in the production of the food of the present invention may be one prepared by any known methods such as a synthetic method or a fermentation method. Moreover, it does not matter whether it is a solid, a solution, a crystalline, or an amorphous product. It is also possible to utilize a ubiquinone on the market for use as supplements.

The ubiquinone for use in the production of the food according to the present invention is not particularly restricted in purity, but may for example preferably have a purity in not less than 0.01%, more preferably not less than 1%, and most preferably not less than 10%. Moreover, not only purified products but also crude products can be used. Generally, purified ubiquinone is expensive and any food enriched with these becomes necessarily costly but the use of a crude ubiquinone enables production of ubiquinone-enriched foods at low cost. Moreover, any food is intrinsically a heterogenous system of a broad variety of substances and, therefore, the ubiquinone to be added needs not to be a purified product provided that it is a safe one. As examples of the crude product mentioned above, there may be mentioned partially purified products obtained by crystallization, solvent extraction, column chromatography, or the like. To cite an example of such crude product, the ubiquinone occurring in ubiquinone-containing microbial cells can be used. As examples of the microorganisms containing ubiquinone, there may be mentioned yeast, fungi, bacteria, algal protozoa, and the like.

The ubiquinone for use in the practice of the present invention is a substance occurring not only in animals and plants but also in many kinds of foodstuffs, and its safety has been confirmed. When a crude ubiquinone preparation is used or ubiquinone-containing microbial cells are used, a sterilization or other procedure may be carried out for preventing contamination with harmful agents for purposes of safety and hygiene and/or a cell disruption or the like procedure may be carried out for improving absorption.

The processes for producing some representative foods of the present invention are described below.

The edible oils/fats of the present invention can be produced by using any of oils/fats which are commonly used as edible oils/fats, for example various vegetable oils such as rapeseed oil, soybean oil, sunflower seed oil, cottonseed oil, peanut oil, rice bran oil, corn oil, safflower oil, olive oil, kapok oil, sesame oil, evening primrose oil, palm oil, shea butter, sal fat, cacao butter, coconut oil, and palm kernel oil, and various animal oils/fats such as milk fat, beef tallow, lard, fish oil, and whale oil; various processed oils/fats derived from the above oils by hydrogenation, interesterification or the like; medium-chain fatty acid triglycerides (MCT) such as triglycerides of fatty acids containing 6 to 12 carbon atoms, preferably 8 to 12 carbon atoms; partial glycerides (monoglycerides and diglycerides) of fatty acids, such as monoglycerides and diglycerides of fatty acids containing 6 to 18 carbon atoms, preferably 6 to 12 carbon atoms; mixtures thereof; and the like. More particularly, the cooking oil can be produced by a process which comprises melting such oil/fat as above at a temperature not below its melting point, adding and dissolving a predetermined amount of ubiquinone in the oil/fat gradually under stirring so as not to be inhomogeneous, and finally cooling the resulting solution.

The spray oil according to the present invention can be produced by using an edible oil/fat same as that for use in the production of said cooking oil in the same process. Optionally, for imparting a flavor to the spray oil, there may be incorporated any of various oil-soluble flavoring ingredients, oil-soluble vitamins, seasoning oils, preservatives, and other food ingredients such as salt, animal meat, poultry meat, fish meat, cream, butter, chicken, onion, garlic, basil, etc. by blending or dissolving with a conventional mixer. When the spray oil according to the present invention is used, it can be used in the same manner as ordinary spray oils.

The butter of the present invention may be produced by the process which comprises churning a cream fraction obtained from cow's milk in the conventional manner under the usual conditions, adding a predetermined amount of a ubiquinone powder or a solution or uniform dispersion of ubiquinone in an edible oil/fat gradually thereto under continued churning, washing the resulting butter particles with cold water, adding about 2.5% of common salt, and further churning the mixture.

The margarines and shortenings of the present invention can be produced by the process which comprises subjecting an oil/fat, which is used in the production of standard margarines and shortenings, and ubiquinone to mixing/dissolving/stirring and, optionally, further to emulsification. An exemplary process for the production of a margarine according to the present invention comprises feeding an ordinary edible oil/fat, a solution of ubiquinone in edible oil/fat medium, water, an emulsifier, and various optional additives to an emulsification tank to effect emulsification at 60° C. and quenching the resulting emulsion to 15° C. under kneading. A margarine may also be produced, for example, by feeding an ordinary edible oil/fat and a finely divided powder of purified ubiquinone or crude ubiquinone concurrently and treating the mixture in the same manner as above. On the other hand, a shortening can be produced by a process which, for example, comprises adding a ubiquinone-enriched oil/fat to an ordinary edible oil/fat, emulsifying the mixture by a homomixer at 60° C. for about 20 minutes, and quenching the emulsion to 15° C. under kneading.

The synthetic cream of the present invention can be produced by a process which comprises mixing a predetermined amount of said solution or dispersion of ubiquinone in edible oil/fat medium with a high-melting point oil such as hydrogenated rapeseed oil and hydrogenated coconut oil, and an emulsifier, warming the mixture for dissolving at about 70° C. with stirring to prepare an oil phase, adding this oil phase to an aqueous phase separately prepared by emulsifying a mixture of skim milk, dissolved salt, an emulsifier, etc. under warming at about 70° C., incubating the mixture at about 65° C. for preliminary emulsification, feeding this mixture to a homogenizer for homogenization under pressure, sterilizing the same, subjecting it further to pressure homogenization, cooling the homogenate to about 5° C., and incubating it for aging at 5° C. for about 24 hours.

The concentrated milk of the present invention can be produced by a process which comprises pooling a predetermined amount of said solution or dispersion of ubiquinone in edible oil/fat medium with an aqueous phase prepared by dissolving nonfat milk solids, nonfat milk component with taste, a thickener, and an emulsifier in water, emulsifying the whole mixture with a homogenizer, and subjecting it to sterilization and homogenization.

The whiteners of the present invention can be produced by a process which comprises mixing a predetermined amount of said solution or dispersion of ubiquinone in edible oil/fat medium with an emulsifier for emulsification to prepare an oil phase and stirring it together with an aqueous phase prepared by dissolving a nonfat milk powder, dissolved salt, a thickener, an emulsifier, a sweetener, vitamins, an antioxidant, etc. for preliminary emulsification and subjecting the whole mixture to pressure homogenization.

The salad dressing of the present invention can be produced by using a predetermined amount of said solution or dispersion of ubiquinone in edible oil/fat medium as the oil/fat to be added. Taking a mayonnaise as an example, it can be produced by mixing and stirring suitable amounts of vinegar, common salt, sugar, condiments, and water in a mixer or the like to prepare an aqueous phase and adding an oil phase separately prepared by mixing said solution or dispersion of ubiquinone in edible oil/fat medium with an emulsifier such as egg yolk portion-wise to said aqueous phase with stirring for preliminary emulsification and feeding the resulting pre-emulsion to a colloid mill or the like for finish-emulsification. Moreover, it can also be produced by adding a solid form of ubiquinone to the edible oil/fat and other ingredients which are used in ordinary dressings and stirring the mixture for emulsification.

The pickling liquor of the present invention can be produced by using said solution or dispersion of ubiquinone in edible oil/fat medium as the oil/fat to be added. As an alternative, a solid form of ubiquinone may be added to the edible oil/fat and other ingredients which are used in the production of ordinary pickling liquors. For example, an oil phase prepared by heating said solution or dispersion of ubiquinone in edible oil/fat medium and an emulsion stabilizer at 60° C. with stirring is added gradually to an aqueous phase separately prepared by dissolving an emulsifier in water under heating to 60° C. with stirring for crude emulsification, and after the temperature of this pre-emulsion has fallen to 50° C. or below, it is further treated with a homogenizing machine such as a pressure homogenizer for fine emulsification. Then, this emulsion is quenched with a heat exchanger such as a plate cooler.

The chocolate of the present invention can be produced by a process which comprises mixing confectionery chocolate with a predetermined amount of a solid form of ubiquinone or a solution of ubiquinone in edible oil/fat medium, stirring the mixture gradually in a water bath at 40 to 50° C., and after complete dissolution, cooling it to 30 to 32° C. Optionally, it can be poured into molds and allowed to solidify.

The breads, cakes, and pies according to the present invention are not particularly restricted in the respective production methods. Thus, at the stage of adding an oil/fat in the general course of production of breads, cakes or pies, a predetermined amount of said solution or dispersion of ubiquinone in edible oil/fat medium may be added in lieu of a portion or the whole of said oil/fat; as an alternative, said margarines or shortenings enriched with ubiquinone be substituted for a portion or the whole of said oil/fat. As a further alternative, the ubiquinone in solid form or in the state occurring in microbial cells may be added simultaneously with addition of an ordinary oil/fat or together with a food ingredient. When ubiquinone-enriched bread is produced, it is preferable to add 1 to 40% of oils/fats in the total weight of the bread. If the content is below 1% or in excess of 40%, flavor and texture of the bread may become poor.

The roux of the present invention can be produced by a process wherein, at the stage of adding an oil/fat in the routine course of production of a roux, a predetermined amount of said solution or dispersion of ubiquinone in edible oil/fat medium is added in lieu of a portion or the whole of said oil/fat; said ubiquinone-enriched margarine or shortening is added in lieu of a portion or the whole of said oil/fat; or ubiquinone in solid form or in the state occurring in microbial cells is added simultaneously with addition of an ordinary oil/fat or together with an oil-rich food ingredient, and after addition of other food ingredients and additives, the whole mixture is heated. The method of heating may be whichever of a treatment with saturated steam, a heating under pressure and, a decoction, and a heating at atmospheric pressure inclusive of oil decoction, and the like. However, the oil decoction is expedient and, therefore, advantageous and this treatment can be carried out at a temperature of 110° C. to 120° C. for a brief time in cases where the roux is not to be colored; at an ultimate temperature of 140° C. to 150° C. in cases where a cream-colored roux is to be produced; or at an ultimate temperature of 190° C. for a sufficient time in cases where a brown roux is to be produced.

The noodles of the present invention can be produced by a process wherein, at the stage of adding an oil/fat in the general course of production of noodles, a predetermined amount of said solution or dispersion of ubiquinone in edible oil/fat medium is added in lieu of a portion or the whole of said oil/fat; said ubiquinone-enriched margarine or shortening is added in lieu of a portion or the whole of said oil/fat; or ubiquinone in solid form or in the state occurring in microbial cells is added simultaneously with addition of an ordinary oil/fat or together with a food ingredient. An exemplary production protocol comprises adding and dissolving an emulsifier in said solution or dispersion of ubiquinone of the present invention in edible oil/fat medium under heating to prepare an oil phase, adding this oil phase with an aqueous phase separately prepared by heating water, sugar, etc., emulsifying the resulting mixture with a mixing machine such as a homomixer, further emulsifying the emulsion under stirring and mixing, blending this emulsion with wheat flour or the like to prepare a dough, allowing it to ripen, rolling the dough, cutting it into ribbons to give raw noodles, and either drying or boiling them.

The fried foods of the present invention can be prepared by a process which comprises frying the food ingredient for croquettes, fried prawn, pork cutlets, or the like using said solution or dispersion of ubiquinone in edible oil/fat medium according to the present invention, said ubiquinone-enriched cooking oil of the present invention, or said ubiquinone-enriched shortening of the present invention, at a high temperature of, for example, 150° C. to 220° C.

The cheese-food and cheese-like food of the present invention can be produced by the conventional methods for producing cheese-food and cheese-like food except that a solution or dispersion of ubiquinone in edible oil/fat medium of the present invention is used. In this connection, said solution or dispersion of ubiquinone in edible oil/fat medium of the present invention may be added either alone or as formulated with any other oils/fats of common use in the art at the stage of adding an oil/fat in the general production sequence. For example, a ubiquinone-enriched cheese-food can be obtained by a process which comprises charging a container such as Stephan cooker with natural cheese or processed cheese, a ubiquinone-enriched edible oil/fat composition of the present invention, common salt, dissolved salt, and water according to a predetermined recipe, warming and kneading the mixture under introduction of steam, and cooling the same. A processed cheese-food, for instance, can be produced by a process which comprises charging a kettle such as Stephan cooker with less than 51%, based on the total weight of food, of natural cheese or processed cheese, a solution or dispersion of ubiquinone in edible oil/fat medium according to the present invention, common salt, dissolved salt such as sodium polyphosphate, and water according to a predetermined recipe, heating the contents by direct introduction of steam under stirring for melting, kneading and placing the mixture in a vessel, and cooling the same therein. An imitation cheese can be produced by a process which comprises charging a kettle with water, dissolved salt, and common salt, heating them to prepare a solution, adding a defatted protein such as rennet-precipitated casein and skim milk powder and a thickener such as rice starch, corn starch, gum Arabic, and carrageenan, stirring the mixture under heating, further adding an acidulant or the like and water, stirring the whole under heating, adding the ubiquinone-enriched edible oil/fat composition of the present invention, stirring the mixture under heating, further adding cheese flavor, a color, an antioxidant, etc., kneading the whole mixture, and finally treating it with a high-pressure homogenizer.

The beverage of the present invention can be produced by dispersing, emulsifying, or dissolving the solution or dispersion of ubiquinone in an edible oil/fat medium of the present invention uniformly and adding the same to the beverage material. As the beverage material, there may be mentioned cow's milk, special cow's milk, sterilized goat's milk, processed milk, fermented milk, coffee drinks, black tea drinks, fruit juice drinks, carbonated drinks, fruit drinks, milk-containing drinks, vegetable juices, soy milk, coconut milk, cream, and the like. Referring, further, to the beverage of the present invention, when the solution or dispersion of ubiquinone in edible oil/fat medium of the present invention is used, the objective beverage can also be produced by preparing a W/O emulsion from said oil/fat and either using it as such or adding it to a relevant beverage material. For example, an emulsifier, an emulsion stabilizer and a hydrophilic antioxidant are added to water and dispersed therein by stirring and this dispersion is heated to prepare a solution. On the other hand, an emulsifier and a lipophilic antioxidant are added and dispersed in said solution or dispersion of ubiquinone in edible oil/fat medium according to the present invention and this dispersion in oil prepared by stirring is heated to prepare a solution. The method for emulsification is not particularly restricted and there may be mentioned the various methods in common use, namely the method which comprises pouring an oil phase into an aqueous phase and emulsifying the mixture mechanically by stirring or application of a pressure, and the membrane-emulsification method which comprises extruding an oil phase into an aqueous phase through microscopic orifices of a membrane, or the like method. By whichever of these methods, an emulsion having sufficiently satisfactory characteristics can be obtained. While the emulsion thus obtained may be used as it is for emulsion-containing beverages, it may be sterilized where long-term storage in emulsion form is required. The temperature, duration and other factors necessary for sterilization are not particularly restricted but when the pH is neutral, UHT sterilization at 120 to 140° C. for 4 to 30 seconds is recommended. The sterilized emulsion is aseptically filled into sterile vials and stored under refrigerator conditions. The mixing level of the emulsion in the beverage material is not particularly restricted but may be 1 to 80%, preferably 2 to 50%, in the emulsion-containing beverage. If the mixing level is below 1%, a homogeneous system may not be easily maintained. If it exceeds 80%, the formulation is not acceptable in terms of flavor and cost. The emulsion-containing beverage thus obtained is optionally subjected to pH adjustment and addition of an antibacterial agent and a sweetener, filled into heat-sterilizable containers such as cans, bottles, or pouches, sealed, and subjected to retort-sterilization at 120 to 126° C. for 15 to 60 minutes.

Regarding other foods according to the present invention, too, the production processes are not particularly restricted. Thus, at the stage of adding an oil/fat in the general course of production, a predetermined amount of said solution or dispersion of ubiquinone in edible oil/fat medium may be added in lieu of a portion or the whole of said oil/fat or said ubiquinone-enriched margarine or shortening may be added in lieu of a portion or the whole of said oil/fat. As a further alternative, ubiquinone in solid form or in the state occurring in microbial cells may be added simultaneously with addition of an ordinary oil/fat.

BEST MODE FOR CARRYING OUT THE INVENTION

The following examples are intended to illustrate the present invention in further detail and should by no means be construed as defining the scope of the present invention. It should be understood that all "parts" and "%" are "parts by weight" and "% by weight".

Example 1

Production of a Ubiquinone-Enriched Cooking Oil
(1)

A 5 L-beaker was charged with 999 g of soybean oil (brand name: Soybean Golden Salad Oil, Yoshihara Oil Mill, Ltd., melting point: 0° C. or below) and while the oil was gently stirred at room temperature, 1 g of ubiquinone (product of Kaneka Corporation, purity: 99.2%) was added in small portions so as not to be inhomogeneous and the mixture was further stirred gently for dissolving to give a cooking oil enriched with 0.1% of ubiquinone. The oil thus obtained was transparently orange and had a rich flavor, being fully qualified for use as frying oil or roasting oil.

Example 2

Storage Stability of a Ubiquinone-Enriched Cooking Oil

The soybean oil enriched with 1% of ubiquinone as obtained in Example 1 was dispensed into two transparent glass bottles. To one of the bottles, 0.1% of an ascorbyl palmitate-d-α-tocopherol combination preparation (brand name; Riken EC-100, product of Riken Vitamin Co., Ltd.) and 0.1% of astaxanthin (brand name; Astax-S, product of Itano Shokken K. K.) were added, and the other bottle was used as a control without any addition. Each bottle was allowed to stand at room temperature in the bright space for four weeks, and the residual amount of ubiquinone was determined on a weekly basis. The assay of ubiquinone was carried out as follows. Each oil/fat was diluted 100-fold with hexane and 10 μl portion of the dilution was analyzed by high-performance liquid chromatography using a YMC-Pack R&D ODS column in accordance with the method for assay of ubidecarenone (another name of ubiquinone) as described in A Commentary on the Pharmacopoeia of Japan, XIII (Hirokawa Shoten, 1996). As a result, whereas the amount of ubiquinone in the control cooking oil decreased to about 60% in 30 days, not less than 75% of the ubiquinone remained in the cooking oil formulated with said ascorbyl palmitate-D-α-tocopherol combination preparation and astaxanthin, and the addition effect of the antioxidant and edible color was confirmed.

Example 3

Production of a Margarine

In a 5 L-beaker, 99% of the hydrogenated cottonseed oil composition (brand name: Snowlite, product of Kaneka Corporation, melting point: 32° C.) and 1% of ubiquinone (product of Kaneka Corporation, purity: 99.2%) were gently stirred for dissolution under warming at 60 to 65° C., and 83.5 parts of the resulting oil composition and 16.5 parts of water were stirred together for emulsification in an emulsification tank at 60 to 65° C. for 15 minutes and, then, quenched to 15° C. by kneading to give a ubiquinone-enriched margarine which was fully acceptable in flavor and physical properties. Furthermore, after quenching to 10° C. by kneading, the resultant was passed through a resting tube and molded with a sheet molder to obtain a margarine for fold-up use. Neither of the margarines showed the unevenness of color, which would result from localization of ubiquinone, whether on the surface or in the internal layer.

Example 4

Production of a Fat Spread

As an aqueous phase composition, 2 parts of gelatin, 1.5 parts of common salt, and 44 parts of water were warmed to 60° C. As an oil phase composition, 25 parts of hydrogenated soybean oil (melting point: 40° C.) warmed to 60° C., 15 parts of soybean oil (bland name: Soybean Golden Salad Oil; product of Yoshihara Oil Mill, Ltd., melting point: 0° C. or below), 0.5 parts of ubiquinone, 0.3 parts of monostearate, 0.2 parts of lecithin, 0.02 parts of vitamin A, 0.002 part of β-carotene, and 0.3 parts of tocopherol were admixed and warmed to 60° C. The aqueous phase was gradually added to this oil phase under stirring to give an emulsion. Using a combinator, this emulsion was quenched to give a ubiquinone-enriched fat spread. This fat spread was not much different from the ordinary fat spread in properties and stability except for a color resulting from ubiquinone and, in addition, had a smooth mouth-feel and a good flavor. Furthermore, it showed no unevenness of color, which would result from localization of ubiquinone, whether on the surface or in the internal layer.

Example 5

Production of a Shortening 60 parts of hydrogenated soybean oil (melting point: 40° C.), 40 parts of rapeseed oil (melting point: 0° C. or below), 5 parts of purified intermediate in production of ubiquinone (ubiquinone purity: 80%), 0.3 parts of lecithin, 0.3 parts of monostearate, and 5 ppm of vitamin E as an antioxidant were homogenized together using a homomixer at 60° C. for 15 minutes. The emulsion was quenched to 15° C. by kneading to give a ubiquinone-enriched shortening which was fully acceptable in flavor. The shortening showed no unevenness of color, which would result from localization of ubiquinone, whether on the surface or in the internal layer.

Example 6

Production of White Bread

To 70 parts of wheat flour were added 2 parts of yeast and 0.1 parts of yeast food, followed by addition of 40 parts of water and blending with a mixer to prepare a sponge dough (kneading temperature: 24° C.). After 4 hours of preliminary fermentation, 30 parts of wheat flour, 5 parts of sugar, 6 parts of the ubiquinone-enriched margarine produced in Example 3, 2 parts of common salt, 3 parts of skim milk powder, and 23 parts of water were added thereto to prepare a finished dough. After a fermentation time of 25 minutes, the dough was divided into pieces. After a bench time of 25 minutes, each dough piece was shaped and the pieces were subjected to second fermentation at 38° C. for 50 minutes and baked at 180° C. for 35 minutes to prepare white breads. The white bread thus obtained was good in flavor and color. In addition, the bread showed no unevenness of color, which would result from localization of ubiquinone, whether on the surface or in the internal layer.

Comparative Example 1

Production of White Bread

To 70 parts of wheat flour were added 2 parts of yeast, 0.1 parts of yeast food, and 0.5 parts of ubiquinone (product of Kaneka Corporation, purity: 99.2%), followed by addition of 40 parts of water and blending with a mixer to prepare a sponge dough (kneading temperature: 24° C.). After 4 hours of preliminary fermentation, 30 parts of wheat flour, 5 parts of sugar, 6 parts of a commercially available margarine (product of Kaneka Corporation, Neo Margarine), 2 parts of common salt, 3 parts of skim milk powder, and 23 parts of water were added thereto to prepare a finished dough. After a fermentation time of 25 minutes, the dough was divided into pieces. After a bench time of 25 minutes, each dough piece was shaped and the pieces were subjected to second fermentation at 38° C. for 50 minutes and baked at 180° C. for 35 minutes to prepare white breads. The bread partly showed unevenness of yellow color, which would result from localization of ubiquinone in the internal layer.

Example 7

Production of Table Bread Rolls 70 parts of hard flour, 2 parts of white superior soft sugar, 2.5 parts of yeast, 0.1 parts of yeast food, and 40 parts of water were admixed and kneaded at a kneading temperature of 24.5° C. for 4 minutes. Then, a fermentation at 30° C. was carried out for 3 hours to prepare a sponge dough. Then, 20 parts of hard flour, 10 parts of soft flour, 10 parts of white superior soft sugar, 1.6 parts of common salt, 3 parts of skim milk powder, 15 parts of the ubiquinone-enriched margarine prepared in Example 3, 12 parts of whole egg, and 6 parts of water were added thereto and the resulting dough was kneaded at 28° C. for 6 minutes. Then, a fermentation at room temperature with a fermentation time of 40 minutes was carried out. The dough was divided into pieces and, after a bench time of 10 minutes, each dough piece was shaped. The pieces were subjected to second fermentation at 38° C. for 50 minutes and baked at 245° C. for 11 minutes to produce table bread rolls. The table bread rolls thus obtained was good in flavor and color, and showed no unevenness of color, which would result from localization of ubiquinone, whether on the surface or in the internal layer of the breads. One of the bread rolls thus prepared was crushed with a coffee mill and extracted twice with 10-volumes of n-hexane. The extract was filtered through a No. 2 filter paper and the filtrate was concentrated under reduced pressure at 40° C. The residual oil fraction thus obtained was diluted with n-hexane and the ubiquinone content was determined by the same procedure as in Example 2. As a result, bread weighing 34 g per roll was found to contain 15.3 mg of ubiquinone/roll.

Example 8

Production of a Chocolate

Using 22.5% of cacao butter (melting point: 35° C.), 0.2% of ubiquinone (product of Kaneka Corporation, purity: 99.2%), 52.0% of powdered sugar, 15.0% of cacao mass, 14.0% of whole milk powder, and 0.3% of lecithin, a molded chocolate was prepared by the routine production method comprising mixing, rolling, conching, and tempering. A chocolate could, thus, be obtained without a viscosity trouble at depositing or a trouble in mold release. Moreover, the chocolate showed no unevenness of color, which would result from localization of ubiquinone, whether on the surface or in the internal layer.

Example 9

Production of Pound Cakes

First, 405 g of the ubiquinone-enriched margarine prepared in Example 3 and 405 g of white superior soft sugar were whipped to a specific gravity of 0.65 and, then, 405 g of whole egg was added in 5 installments and admixed. Then, 450 g of sieved soft flour was added on top of the above mixture, followed by further mixing. The resulting batter, 500 g, was placed in pound-cake molds and baked at 240° C. for 33 minutes to produce pound cakes. The pound cakes thus obtained were good in taste and texture. The cakes showed no unevenness of color, which would result from localization of ubiquinone, whether on the surface or in the internal layer.

Example 10

Production of Cookies 600 g of soft flour, 250 g of white superior soft sugar, 240 g of the ubiquinone-enriched margarine prepared in Example 3, 30 g of sweetened condensed milk, and 3 g of common salt were emulsified by stirring until a suitable consistency had been obtained. Then, 4 g of ammonium carbonate was dissolved in 30 g of water and gradual emulsification was carried out at a medium speed. Then, 600 g of sieved soft flour was added, the resultant was stirred, the dough was rounded off and let stand for 24 hours. Using a sheeter, the dough was spread out to 5 mm in thickness, stamped out using the chrysanthemum flower-shaped cutter with a diameter of 4 cm, arranged on a baking tray, and baked at 220° C. for 10 minutes to produce cookies. The coolies thus obtained were good in both taste and texture. The cookies showed no unevenness of color, which would result from localization of ubiquinone, whether on the surface or in the internal layer. The ubiquinone content in the obtained cookies was determined in the same manner as Example 7, and the result showed that a cookie (7.6 g) contained 0.45 mg of ubiquinone.

Example 11

Production of a Whipped Cream

In a mixed oil composed of 70 parts of hydrogenated rapeseed oil having a melting point of 34° C. and 30 parts of hydrogenated coconut oil having a melting point of 32° C. were dissolved 0.8 parts of synthetic diglycerol stearate, as an emulsifier, 0.6 parts of soybean lecithin, 0.5 parts of ubiquinone (product of Kaneka Corporation, purity: 99.2%) at an oil temperature of 70° C. to prepare an oil composition. Separately, 0.1 parts of sodium hexametaphosphate was added to 54.9 parts of skim milk and the whole was warmed to 55° C. with stirring. To this skim milk was added 45 parts of the above oil composition to which emulsifier was added, and the whole mixture was stirred for dissolving. With this solution being maintained at 65° C., a preliminary emulsification was carried out. The mixture obtained was fed to a homogenizer for homogenization under the pressure of 80 kg/cm$^2$ for a first run and the pressure of 20 kg/cm$^2$ for a second run. Thereafter, it was sterilized at 95° C. for 15 seconds, and using a plate cooler, it was cooled to 5° C., followed by 24 hours' aging in an incubator at 5° C., whereby a ubiquinone-enriched synthetic whipped cream could be obtained. The thus-prepared cream was fully acceptable in flavor, and showed no unevenness of color which would result from localization of ubiquinone. The thus-prepared synthetic whipped cream was coated on top of a sponge cake prepared in advance to provide a fancy cake.

Example 12

Production of a Concentrated Milk

To 10 parts of soybean oil (brand name: Soybean Golden Salad Oil; product of Yoshihara Oil Mill, Ltd., melting point: 0° C. or below) were added 0.1 parts of lecithin and 0.5 parts of ubiquinone, and the mixture was heated for dissolving at 65° C. for use as an oil phase. Separately, 25 parts of skim milk powder, 0.1 parts of glycerol fatty acid ester, and 0.1 parts of sucrose fatty acid ester were dissolved in 64.2 parts of water at 60° C. to prepare an aqueous phase. The above oil phase was combined with this aqueous phase and the mixture was emulsified with a homogenizer. The emulsion obtained was sterilized at 145° C. for 4 seconds, then subjected to pressure homogenization under 200 kg/cm$^2$, then cooled, and filled into a container to give a ubiquinone-enriched concentrated milk for processing use which had a rich flavor with the mellow taste and body of oil retained. The concentrated milk showed no unevenness of color which would result from localization of ubiquinone.

Example 13

Production of Milk Bread

To 70 parts of wheat flour were added 2 parts of yeast and 0.1 parts of yeast food, followed by addition of 40 parts of water and blending with a mixer to prepare a sponge dough (kneading temperature: 24° C.). After 4 hours of preliminary fermentation, 30 parts of wheat flour, 5 parts of sugar, 6 parts of a commercially available margarine (product of Kaneka Corporation, Neo Margarine), 2 parts of common salt, 3 parts of skim milk powder, 8 parts of the concentrated milk obtained in Example 12, and 15 parts of water were added thereto to prepare a finished dough. After a fermentation time of 25 minutes, the dough was divided into pieces. After a bench time of 25 minutes, each dough piece was shaped and the pieces were subjected to second fermentation at 38° C. for 50 minutes and baked at 180° C. for 35 minutes to prepare milk breads. The bread showed no unevenness of color, which would result from localization of ubiquinone, whether on the surface or in the internal layer.

Example 14

Production of a White Sauce and Production of Pizza Pies and a Gratin-Filled Buns To the white sauce roux prepared by frying 100 g of wheat flour with 100 g of the ubiquinone-enriched margarine prepared in Example 3 was added 800 g of a two-fold aqueous dilution of the ubiquinone-enriched concentrated milk for processing use (400 g) as produced in Example 12, supplemented with 1.0 g of common salt and spice, and the roux was diluted under stirring and heating at an ultimate temperature of 85° C. to produce a white sauce. This sauce was filled into cans and heat-treated with a retort sterilizer at 121° C. for 20 minutes, followed by cooling to room temperature to provide a retort white sauce. The white sauce thus obtained was good in both flavor and texture.

Meanwhile, to 100 parts of the above white sauce prior to said retort sterilization were added 10 parts of blanched chicken, 0.2 parts of yeast extract, and 0.6 parts of chicken soup stock to prepare a chicken gratin. When this was used as a pizza topping and a filling for dainty-filled buns, pizza pies and gratin-filled buns as tasteful as the conventional products were obtained.

Example 15

Production of a Whitener

After 360 parts by weight of soybean oil (brand name: Soybean Golden Salad Oil, product of Yoshihara Oil Mill, Ltd., melting point: 0° C. or below) was warmed to 65 to 70° C., 7.2 parts by weight of soybean lecithin, 4.5 parts by weight of sucrose fatty acid ester (HLB=1), and 10 parts of ubiquinone (product of Kaneka Corporation, purity: 99.2%) were respectively added and dissolved to prepare an oil phase.

Separately, 57.6 parts by weight of skim milk powder, 81 parts by weight of sodium caseinate, 40 parts by weight of trehalose (brand name: Trehaose; distributed by Hayashibara Shoji, INC.), 18 parts by weight of sucrose, 1.8 parts by weight of the hydrophilic emulsifier polyglycerol fatty acid ester (brand name: Poem 0081 H (HLB=14); distributed by Riken Vitamin Co., Ltd.), 3.6 parts by weight of sucrose fatty acid ester (HLB=15), 5.4 parts by weight of disodium hydrogenphosphate, and 3.6 parts by weight of dipotassium hydrogenphosphate were respectively added and dissolved in 1,212.3 parts by weight of hot water at 65 to 70° C. to prepare an aqueous phase. These aqueous phase and oil phase were fed to a homogenizer for preliminary emulsification under stirring and heating at 65 to 70° C. for 15 minutes. Then, the pressure to be applied was varied in two stages (first stage; 180 kg/cm$^2$, second stage; 50 kg/cm$^2$) for further homogenization. Then, the homogenate was transferred to a UHT sterilizer, in which it was heated and sterilized at 145° C. for 2 seconds. The sterilized homogenate was further transferred to a sterile homogenizer in which it was further homogenized at 70° C. under the pressure varied in two stages (first stage: 100 kg/cm$^2$, second stage; 50 kg/cm$^2$) to prepare a ubiquinone-enriched whitener which was fully acceptable in flavor. The whitener showed no unevenness of color, which would result from localization of ubiquinone.

Example 16

Production of a Custard Cream

Two egg yolks were beaten in a pan and, out of 200 ml of a two-fold aqueous dilution of the ubiquinone-enriched concentrated milk produced in Example 12 (100 ml), 2 tablespoon-levels were added and admixed using a wooden spatula. Then, 2 tablespoonfuls of wheat flour and 40 g of sugar were added and thoroughly blended. The rest of the above concentrated milk dilution was added gradually and mixed evenly so as not to be inhomogeneous and boiled at 90° C. for 30 minutes with stirring until a creamy consistency had been obtained. After the mixture was allowed to cool for a brief time, vanilla essence was added and the whole was stirred well to prepare a ubiquinone-enriched custard cream with a rich flavor. The custard cream showed no unevenness of color, which would result from localization of ubiquinone.

Example 17

Production of Cream Puffs

In an emulsification tank, 50 parts of an oil composition prepared from soybean oil (brand name: Soybean Golden Salad Oil, product of Yoshihara Oil Mill, Ltd., melting point: 0° C. or below) 20%, hydrogenated soybean oil (melting point: 40° C.) 60%, and palm oil (melting point: 28° C.) 20%, 1 part of ubiquinone, 0.3 parts of lecithin, 0.3 parts of monoglyceride, 16 parts of water, 2 parts of common salt, and 5 ppm of vitamin E as an antioxidant were emulsified in an emulsification tank by stirring at 60° C. for 15 minutes. The resulting emulsion was quenched to 15° C. and mixed to give a ubiquinone-containing margarine. Then, 130 g of the above margarine and 130 ml of a two-fold dilution of 65 ml of the ubiquinone-enriched concentrated milk prepared in Example 12 were put in a pan and heated at 50° C. to melt the margarine and when the margarine had melted completely and the mixture began to boil, 800 g of sieved soft flour was added and mixed to dextrinize the starch. Then, 200 ml of whole egg was added in several portions and blended thoroughly. In the last stage where whole egg was added, 0.5 g of ammonium carbonate dissolved thoroughly in whole egg was added. Then, a squeeze bag fitted with a circular nozzle, 10 cm in diameter, was filled with the dough and the dough was squeezed out to make round dough pieces on a sheet of paper spread on an iron plate. Using a handy atomizer, the dough pieces were thoroughly exposed to a mist of water, set on the lower shelf of an oven heated at 200° C., and baked for 10 minutes. After sufficient distension was attained, the dough pieces were further baked at 170° C. to produce puff shells. After baking, the shells were allowed to cool on a wire-mesh screen. A crosswise slit was made in each puff shell at the level of about ⅓ from top and a custard cream prepared in Example 16 was inserted via the slit to produce ubiquinone-enriched cream puffs which were fully acceptable in flavor and texture. The cream puffs showed no unevenness of color, which would result from localization of ubiquinone.

Example 18

Preparation of Chocolate Bavarois

First, 250 ml of a two-fold dilution of the concentrated milk produced in Example 12 and 20 g of sugar were put in a pan and heated. The fire was turned off just before boiling and the mixture was added portion-wise to a whipped mixture of 2 egg yolks and 20 g of sugar prepared in advance and the whole was stirred and heated over a low flame. Then, 6 g of gelatin reconstituted with water was added and the mixture was stirred and added through a filter portion-wise into a bowl containing 50 g of chocolate. After stirring the mixture obtained, 100 ml of the cream prepared in Example 11 was beaten and added thereto in 3 divided portions, and the whole was stirred. The mixture was poured into pudding molds and chilled well in the refrigerator to give a ubiquinone-enriched chocolate bavarois with a rich flavor. The chocolate bavarois showed no unevenness of color, which would result from localization of ubiquinone.

Example 19

Production of a Curry Roux 39 parts of a roast flour prepared by using 20 parts of wheat flour and 20 parts of soybean oil (brand name: Soybean Golden Salad Oil, product of Yoshihara Oil Mill, Ltd., melting point: 0° C. or below), 15 parts of edible oil/fat (mixture of lard (melting point: 35° C.) and beef tallow (melting point: 47° C.)), 1 part of ubiquinone, 20 parts of curry powder, 10 parts of common salt, and 15 parts of various condiments such as bouillons were mixed under heating at 90° C. for 30 minutes to prepare a ubiquinone-enriched curry roux. Both the flavor and mouth-feel of the roux were fully acceptable. Neither of the curry roux showed the unevenness of color, which would result from localization of ubiquinone.

Example 20

Production of a Béchamel Sauce

First, 100 g of soybean oil (brand name: Soybean Golden Salad Oil, product of Yoshihara Oil Mill, Ltd., melting point: 0° C. or below) was placed in a thick-bottomed pan and, under heating, 100 g of soft flour and 5 g of ubiquinone were added together in one operation. While being careful to prevent burning, the mixture was stirred at 90° C. for 20 minutes using a wooden spoon. Thereafter, the pan was removed from the fire and allowed to cool briefly to obtain a white roux. Then, one cup of cold cow's milk was added and stirred evenly. Then, 1.5 cups of cow's milk at 10° C. was further added and using a beater, the whole was thoroughly stirred until brilliance had begun to appear. Thereafter, 2.5 cups of cow's milk at 10° C. was added and stirred well. Then, a cloves-stabbed onion and bay leaves were added and the whole was boiled down to a pulp-like consistency over a low flame. The bay leaves and onion were taken out, the slurry was filtered through a chinois, and the filtrate was transferred to the pan again and heated over a low flame to the extent just short of burning to produce 550 g of a ubiquinone-enriched béchamel sauce which was good in flavor and texture. The sauce showed no unevenness of color, which would result from localization of ubiquinone.

Example 21

Production of a Mayonnaise 5 parts of vinegar (containing 10% of acetic acid), 2 parts of common salt, 0.5 parts of sugar, 0.3 parts of mustard powder, and 0.2 parts of water were put in a mixer and stirred together at 15° C. to 20° C. to prepare an aqueous phase. Then, an emulsion (10° C. to 15° C.) prepared by stirring 7 parts of egg yolk and 0.5 parts of ubiquinone was added to 68 parts of rice refined oil (shirashime-yu) (melting point: 0° C. or below) portion-wise and the whole was stirred at 15° C. to 20° C. for preliminary emulsification. Then, using a colloid mill, a finish emulsification was performed to produce a ubiquinone-enriched mayonnaise. The mayonnaise obtained was fully comparable to the commercial mayonnaise in taste, body, and mouth-feel. The mayonnaise showed no unevenness of color, which would result from localization of ubiquinone.

Example 22

Production of a French Dressing

In 33.1 parts of water were dissolved 15 parts of vinegar (acetic acid concentration: 10%), 8 parts of sugar, 3 parts of starch, 0.5 parts of pepper, and 0.4 parts of xanthan gum, and the solution was sterilized by heating at 80° C. for 30 minutes, followed by cooling to 20° C. Then, 40 parts of rice refined oil (shirashime-yu) (melting point: 0° C. or below) preliminarily warmed to 10 to 15° C. and 1 part of ubiquinone were added and the whole was stirred at 15 to 20° C. for preliminary emulsification. Then, using a colloid mill, a finish emulsification was carried out to produce a French dressing. The French dressing obtained was good in taste, body, and mouth-feel, and showed no unevenness of color, which would result from localization of ubiquinone.

Example 23

Production of a Potato Salad 5 parts of skinned potato and 1 part of carrot were respectively cut into cubes. These were wrapped up in Saran-wrap and cooked soft in a microwave oven set to the root vegetable cooking mode, followed by cooling. Then, 2 parts of onion slices rinsed in water prepared separately were added and, finally, 2 parts of the ubiquinone-enriched mayonnaise produced in Example 21 was added. The whole was admixed to produce a ubiquinone-enriched potato salad which was good in flavor and mouth-feel.

Example 24

Preparation of an Ice Cream

Egg yolks equivalent to 10 hen's eggs was beaten in a vessel and 250 g of sugar and 10 g of corn starch were added and stirred well. Then, 1 L of a two-fold dilution of the ubiquinone-enriched concentrated milk produced in Example 12 was warmed to 75° C. and mixed in gradually. The whole mixture was filtered through a fine-mesh screen, warmed at 90° C. for 45 minutes, and stirred gently using care not to cause burning until a syrupy consistency had been attained, followed by cooling on ice. After cooling, a small amount of vanilla essence was added and the whole was frozen with stirring at −20° C. When it had begun to solidify, 270 g of the ubiquinone-enriched whipped cream prepared in Example 11 was beaten and added. The whole was further cooled with stirring, distributed into cups, and frozen to obtain a vanilla ice cream with a good flavor and mouth-feel. The vanilla ice cream showed no unevenness of color, which would result from localization of ubiquinone.

Example 25

Preparation of Puddings 1,000 ml of a two-fold dilution of the ubiquinone-enriched concentrated milk produced in Example 12 was warmed up to about 40° C. and blended with a premix of 250 g of sugar and 250 g of whole egg. This pudding pastry was filtered through a strainer, cast into pudding molds, and baked on a water bath in an oven at 150° C. for 30 to 40 minutes to prepare custard puddings with a rich flavor. The custard puddings showed no unevenness of color, which would result from localization of ubiquinone.

Example 26

Production of a Pickling Liquor and Pork Cutlets 5 parts of soybean oil (brand name: Soybean Golden Salad Oil, product of Yoshihara Oil Mill, Ltd., melting point: 0° C. or below), 0.1 parts of sodium caseinate, 0.1 parts of tetrasodium pyrophosphate, 2 parts of common salt, and 0.2 parts of ubiquinone were mixed and stirred, and further 95.6 parts of water were added. Using a pressure homogenizer, the whole was emulsified at 100 kg/cm$^2$ to give a ubiquinone-enriched pickling liquor.

The pork loin for cutlets was injected with 20%, based on meat weight, of the above pickling liquor and, after massage, cut to the bite size, dipped through a batter solution, coated with crumbs, and fried. As a result, there was obtained ubiquinone-enriched pork cutlets which were juicy and had a rich flavor.

Example 27

Production of a Coating Oil/Fat Composition and Butter Rolls 2 parts of beaten eggs was gradually added to 68 parts of water and dispersed with a homomixer, followed by warming to 70° C. Then, an oil composition prepared by dissolving 1 part of ubiquinone in 30 parts of soybean oil (brand name: Soybean Golden Salad Oil, product of Yoshihara Oil Mill, Ltd., melting point: 0° C. or below) in advance was gradually added and the whole was further stirred for 10 minutes, sterilized at 142° C. for 2 seconds, and emulsified with a pressure homogenizer at 100 kg/cm$^2$ to give a ubiquinone-enriched coating oil/fat composition.

The coating oil/fat composition obtained was applied to fermented butter roll doughs, 0.5 g per roll, and baked at 200° C. for 9 minutes to give ubiquinone-enriched butter rolls with good brilliance and flavor.

Example 28

Production of Croquette

The croquette-dough prepared by the conventional procedure was coated with a batter prepared by mixing a batter mix powder (brand name: Batter Mix U-869, product of Riken Vitamin Co., Ltd.), rapeseed oil and water in a ratio of 1:2:4 and, then, with crumbs, and the whole was fried at 170° C. to prepare croquettes. The face and reverse sides of each croquette (about 40 g) were sprayed with 1 g of the coating composition produced in Example 27. The ubiquinone-enriched croquettes thus obtained were very satisfactory in texture and flavor even after frozen storage and recooking with a microwave oven, and showed no unevenness of color, which would result from localization of ubiquinone.

Example 29

Production of Snack Confections 55 parts of corn flour, 13 parts of potato starch, 3 parts of granulated sugar, 0.5 parts of common salt, and 22 parts of water were fed to a twin-screw extruder and, after 7 seconds' residence at a barrel temperature of 140° C., extruded into a spiral form. The resultant was cut at 30 mm pitches to prepare 0.8 mm-thick snack doughs. The snack doughs thus obtained were subjected to 16 hours' preliminary dehydration at 40° C. and, further to a swelling treatment using a conveyor dryer at 260° C. for 26 seconds. 100 g of the swollen doughs were sprayed with 3 g of the coating oil/fat composition obtained in Example 27 to give ubiquinone-enriched snack confections good in flavor, color, and gloss. The snack confections showed no unevenness of color, which would result from localization of ubiquinone.

Example 30

Production of Noodles (Udon)

First, an oil phase composition consisting of 20 parts of soybean oil (brand name: Soybean Golden Salad Oil, product of Yoshihara Oil Mill, Ltd., melting point: 0° C. or below), 2.5 parts of glycerol saturated fatty acid monoester (brand name: Emulsee MS, product of Riken Vitamin Co., Ltd.), 0.8 parts of glycerol unsaturated fatty acid monoester (brand name: Poem OL-200, product of Riken Vitamin Co., Ltd.), 0.05 parts of polyglycerol fatty acid ester (brand name: Poem OL-100A, product of Riken Vitamin Co., Ltd.), 1.5 parts of sucrose fatty acid ester (HLB=1) (brand name: DKF-10, product of Dai-Ichi Kogyo Seiyaku Co., Ltd.), 0.4 parts of lecithin, and 1 part of ubiquinone was stirred and heated for dissolving to prepare an oil phase. On the other hand, an aqueous phase composition of 30 parts of water, 13 parts of reduced starch saccharification product (brand name: Eswee 57 (solids; 75%), product of Nikken Chemicals Co., Ltd.), and 25 parts of sorbitol (brand name: Sorbitol F (solids: 70%), product of Nikken Chemicals Co., Ltd.) was heated under stirring for use as an aqueous phase. Then, these oil phase and aqueous phase were mixed and emulsified with a homomixer, followed by further stirring and mixing to give a ubiquinone-enriched emulsified oil/fat composition. To 3 parts each of the oil emulsion obtained above were added 100 parts of wheat flour and 32 parts of water, and the whole was kneaded, formed, and rolled in the conventional manner. The resulting 2.5 mm-thick dough sheet was divided with a No. 10 cutter blade to give raw noodles. These raw noodles were boiled in boiling water for 7 minutes and the condition and texture of the boiled noodles were evaluated. As the result, it was found that these noodles had a body. Meanwhile, the raw noodles were stored in the refrigerator for 10 days and evaluated in the same manner. It was found that the raw noodles were also fully acceptable in flavor and texture, and unevenness of color, which would result from localization of ubiquinone was not found.

Example 31

Production of a Tea with Milk

In 50 g of a hot water extract of black tea leaves were dissolved 60 g of granulated sugar, 0.5 g of sucrose fatty acid ester, and 1 g of sodium bicarbonate, followed by addition of 50 g of the ubiquinone-enriched concentrated milk for processing use as produced in Example 12, and the whole was diluted to 1,000 ml with water to prepare an emulsion having a rich flavor. This emulsion was heated to 80° C., filled into cans (190 ml), and subjected to retort sterilization at 124° C. for 20 minutes, whereby a canned ubiquinone-enriched tea with milk-beverage having a body characteristic of oil/fat was obtained. The tea with milk showed no unevenness of color, which would result from localization of ubiquinone.

Example 32

Production of Café Au Lait (Coffee with Milk)

50 g of the ubiquinone-enriched concentrated milk for processing use as produced in Example 12 was formulated with 50 g of coffee extract, 60 g of granulated sugar, 0.5 g of sucrose fatty acid ester, and 1 g of sodium bicarbonate and the mixture was emulsified by stirring to prepare a ubiquinone-enriched café au lait which was good in flavor and body. The café au lait showed no unevenness of color, which would result from localization of ubiquinone.

Example 33

Production of a Sour Beverage

To each of 100 g portions of rice refined oil (shirashime-yu) (melting point: 0° C. or below) taken, 130 g of sucrose diacetate hexaisobutyrate, 2 g of ubiquinone, and 1 g of natural vitamin E were mixed and dissolved to obtain a homogeneous oily material mixture. This mixture was added to a solution prepared by mixing and dissolving 615 g of glycerol, 60 g of decaglycerol monooleate (HLB=12), and 135 g of water and dispersed by preliminary stirring. Then, using T. K. Homomixer (manufactured by Tokushu Kika Kogyo Co., Ltd.), the above dispersion was emulsified at 5,000 rpm for 10 minutes to prepare a homogeneous emulsion composition. Separately, 200 g of granulated sugar, 5 g of citric acid, and 0.5 g of vitamin C were dissolved in a suitable quantity of water, and the solution was adjusted to pH 3.0 with sodium citrate and diluted to 2 L with water to prepare a syrup for sour beverage use. To 180 ml each of this syrup, 20 ml each of the above-prepared emulsion was added and mixed, filled into a bottle, capped, sterilized at 85° C. for 15 minutes, and cooled to provide a ubiquinone-enriched sour beverage. The sour beverage showed no unevenness of color, which would result from localization of ubiquinone.

Example 34

Production of a Coffee Beverage 6 g of sucrose fatty acid ester (HLB=16), 8 g of sorbitan fatty acid ester (HLB=7), 1 g of phosphate, 0.5 g of carrageenan, 65 g of sodium caseinate, 38 g of sodium ascorbate, and 550 g of water were admixed and warmed to 60° C. for dissolving. Separately, 200 g of rice refined oil (shirashime-yu) (melting point: 0° C. or below), 100 g of hydrogenated soybean oil (melting point: 40° C.), 2 g of sucrose fatty acid ester (HLB=1), 5 g of ubiquinone, 0.5 g of natural vitamin E, 0.5 g of β-carotene, 0.3 g of lecithin, 0.3 g of tocotrienol, and 0.1 g of sesame lignan were mixed together and warmed to 60° C. for dissolving. To the above aqueous phase maintained at 60° C., this oil phase similarly maintained at 60° C. was added, and the mixture was stirred for preliminary emulsification. Then, the resultant was homogenized under a pressure of 180 kg/cm$^2$ and the resulting homogenate was subjected to UHT sterilization at 120° C. for 20 seconds and filled into a container to give an aseptic emulsion. Then, 50 g of a hot water extract of roast coffee beans, 60 g of granulated sugar, 0.5 g of sucrose fatty acid ester, and 1 g of sodium bicarbonate were added and dissolved. Then, 20 g of the aseptic emulsion obtained above was added and the whole was diluted to 1,000 ml with water to give an emulsion-containing coffee extract. The extract was heated to 80° C., filled into cans (190 ml), and subjected to retort sterilization at 124° C. for 20 minutes to prepare canned ubiquinone-enriched coffee drinks with a good flavor. The coffee drinks showed no unevenness of color, which would result from localization of ubiquinone.

Example 35

Increase of Ubiquinone Concentration in Blood Due to Bread Rolls and Cookies 16 male Crj:CD (SD) rats (body weights 260 g to 300 g) were divided into 4 groups of 4 individuals. The first group (ubiquinone-bread roll group) was fed on the ubiquinone-enriched table bread rolls produced in Example 7 in a daily ration of one roll (30 g); the second group (control bread roll group) was fed on the table bread rolls produced in the same manner as Example 7 except for without adding ubiquinone in a daily ration of one roll (30 g); the third group (ubiquinone-cookie group) was fed on the ubiquinone-enriched cookies produced in Example 10 in a daily ration of 4 pieces (28 g); and the fourth group (control cookie group) was fed on the cookies produced in the same manner as Example 10 without adding ubiquinone in a daily ration of 4 pieces (28 g), with free access to water, for one week.

On the morning of week 1, the blood was withdrawn from the abdominal aorta of each animal under ether anesthesia. To 1.0 ml of the plasma collected, 2.0 ml of water, 4.0 ml of ethanol, 10.0 ml of n-hexane were serially added and the mixture was shaken vigorously for about 5 minutes and then centrifuged for phase separation. The organic solvent layer was recovered and the remaining aqueous layer was subjected to extraction twice with adding 10.0 ml portions of n-hexane. The organic solvent layers obtained were pooled and the solvent was distilled off under reduced pressure to obtain a dry residue. The dry residue was dissolved in 250 μl of ethanol:1 N-hydrochloric acid (99:1, v/v) and a 10 μl portion of the solution was analyzed by high performance liquid chromatography, and the content of ubiquinone was determined. The HPLC parameter settings were as follows: column; YMC-PacK R&D ODS, 250×4.6 mm (manufactured by YMC Co., Ltd.), mobile phase; 0.5 M $NaClO_4/C_2H_5OH$: $CH_3OH$:$CH_3CN$:70% $HClO_4$ (400:300:300:1, v:v), detection wavelength: 275 nm, flow rate: 1 ml/min.

As a result, whereas the blood ubiquinone concentration in the control bread roll group was 0.01 μg/ml on average in 4 rats, the ubiquinone-bread roll group showed an average blood ubiquinone concentration of 0.46 μg/ml, which represents a significant increase in blood ubiquinone concentration. Similarly, whereas the concentration in the control cookie group was 0.01 μg/ml, that in the ubiquinone-cookie group was as high as 0.48 μg/ml. The blood ubiquinone concentration is significantly increased by ingesting ubiquinone-enriched foods, thus it was confirmed that ubiquinone, which is liable to fall short of requirements, can be supplied with ease by ingesting ubiquinone-enriched foods.

INDUSTRIAL APPLICABILITY

The present invention makes it possible to uniformly dissolve or disperse ubiquinone in substrate food and, at the same time, prevent precipitation and localization of the ubiquinone in the food during storage. The food enriched with ubiquinone in such a uniformly dissolved or dispersed state is a food which, by ingesting in the same ways as ordinary foods, enables supplying ubiquinone which is liable to fall short of requirements. It is of use as a food for the prevention or amelioration of the fatigue and various kinds of poor health conditions arising from ubiquinone deficiencies.

The invention claimed is:

1. A process for producing an ordinary food enriched with ubiquinone wherein the ordinary food enriched with ubiquinone is a food in a form other than tablets or capsules, which comprises dissolving ubiquinone in an oil/fat under heating at a heating temperature of not lower than the melting point of ubiquinone, wherein the heating temperature is within the range of 50° C. to 70° C., and adding the obtained mixture to a food material.

2. The process according to claim 1,
   wherein the oil/fat has a melting point of not lower than 20° C., and the mixture to be added to a food material is obtainable by dissolving ubiquinone in said oil/fat under heating, and solidifying or plasticizing the resultant, or preparing the resultant into an oil-in-water emulsion or a water-in-oil emulsion.

3. The process according to claim 1,
   wherein the oil/fat has a melting point of below 20° C., and the mixture to be added to a food material is obtainable by dissolving ubiquinone in said oil/fat under heating, and preparing the obtained mixture into an oil-in-water emulsion.

4. An ordinary food enriched with ubiquinone which is obtainable by the process according to claim 1.

* * * * *